(12) United States Patent
Gerlach et al.

(10) Patent No.: US 6,796,978 B2
(45) Date of Patent: Sep. 28, 2004

(54) MEDICAL LASER THERAPY DEVICE

(75) Inventors: Mario Gerlach, Eisenberg (DE); Martin Wiechmann, Jena (DE); Olaf Kittelmann, Kleinmachnow (DE); Diegeo Zimare, Jena (DE); Michael Kempe, Kunitz (DE); Dirk Muehlhoff, Kunitz (DE); Alexander Kalies, Frauenpriessnitz (DE)

(73) Assignee: Carl Zeiss Jena GmbH, Jena (DE)

( * ) Notice: Subject to any disclaimer, the term of this patent is extended or adjusted under 35 U.S.C. 154(b) by 117 days.

(21) Appl. No.: 10/043,465

(22) Filed: Jan. 10, 2002

(65) Prior Publication Data

US 2002/0177844 A1 Nov. 28, 2002

(30) Foreign Application Priority Data

Jan. 11, 2001 (DE) .......................................... 101 00 859

(51) Int. Cl.[7] .............................................. A62B 18/20
(52) U.S. Cl. .............................. 606/10; 606/4; 606/606; 606/11
(58) Field of Search ............................ 606/4, 6, 10–11, 606/16–18; 372/6, 22, 25, 34

(56) References Cited

U.S. PATENT DOCUMENTS

| | | | | |
|---|---|---|---|---|
| 3,828,788 A | * | 8/1974 | Krasnov et al. ................ | 606/4 |
| 4,477,159 A | * | 10/1984 | Mizuno et al. .............. | 351/221 |
| 4,580,559 A | * | 4/1986 | L'Esperance ................... | 606/3 |
| 5,252,999 A | * | 10/1993 | Sukigara et al. ............. | 351/221 |
| 5,504,762 A | * | 4/1996 | Hutchison ............... | 372/29.011 |
| 5,817,088 A | * | 10/1998 | Sterling ........................... | 606/4 |
| 5,923,684 A | * | 7/1999 | DiGiovanni et al. ............ | 372/6 |
| 5,982,789 A | * | 11/1999 | Marshall et al. ............... | 372/22 |
| 6,327,278 B1 | * | 12/2001 | Toscheck et al. ............... | 372/6 |
| 6,350,031 B1 | * | 2/2002 | Lashkari et al. ............. | 351/221 |
| 6,363,088 B1 | * | 3/2002 | Alphonse et al. ............... | 372/6 |
| 6,530,918 B1 | * | 3/2003 | Ueno et al. .................... | 606/10 |

OTHER PUBLICATIONS

Data Sheets for 532 nm Lasers by JDS Uniphase Company.*

* cited by examiner

*Primary Examiner*—Roy D. Gibson
(74) *Attorney, Agent, or Firm*—Reed Smith LLP

(57) ABSTRACT

A medical laser therapy device, particularly for use in ophthalmology and surgery, comprises a controllable pump module with a coupling element for a waveguide, a beam control device in the form of a waveguide for supplying the pumping radiation delivered by the pump module to the applicator which is provided with a coupling element for the waveguide for introducing a target beam and/or treatment beam into the eye to be treated. The device is primarily characterized in that the pump module has laser diodes whose electromagnetic pumping radiation is in the spectral range from 800 nm to 815 nm, and in that an optics module is provided which couples the pumping radiation into the waveguide, in that the beam control device is an Nd-doped waveguide laser with a double core or single core and a suitable reflecting coating of the fiber end faces, the waveguide forming a laser cavity with radiation in a frequency range between 1050 nm and 1070 nm, in that the applicator is a laser slit lamp with zoom system having a device for frequency doubling which preferably comprises nonlinear optical material or periodically poled nonlinear optical material, in that the applicator has a device for power monitoring and a device for illuminating and observing the operating field, and in that the applicator has a target beam device whose radiation is coupled collinearly into the beam path for the therapy radiation by a suitable beamsplitter. The medical therapy device is constructed in a modular manner.

26 Claims, 2 Drawing Sheets

MEDICAL LASER THERAPY DEVICE

CROSS-REFERENCE TO RELATED APPLICATIONS

This application claims priority of German Application No. 101 00 859.7, filed Jan. 11, 2001, the complete disclosure of which is hereby incorporated by reference.

BACKGROUND OF THE INVENTION a) Field of the Invention

The invention is directed to a medical laser therapy device, particularly for use in surgery and ophthalmology.

b) Discussion of Related Art and Problems Addressed by the Invention

In scarcely any other medical discipline is the use of lasers so established as in ophthalmology, where patients have the very considerable advantage of noninvasive treatment which can usually be performed on an outpatient basis. Alternative methods are often unavailable or involve invasive procedures in the eye.

Almost all of the laser therapy devices currently used in ophthalmology for photocoagulation and photodynamic therapy (PDT) comprise a laser therapy device, an applicator and a beam control system which is usually constructed as a waveguide for optical radiation and which supplies the laser radiation generated by the laser therapy device to the applicator, through which the radiation, as therapy radiation, or the target beam or observation beam generated by another radiation source is directed into the eye to be treated.

Apart from $Ar^+$, $Kr^+$ or mixed-gas lasers whose operation is very cost-intensive and energy-intensive, solid-state type laser systems delivering therapeutic laser radiation of one wavelength are currently employed as radiation sources for photocoagulation and PDT. When different wavelengths of therapy radiation are required for different applications, it is generally necessary to use several laser systems or to refit existing systems in an uneconomical manner. Further, laser slit lamps, with or without special link systems, of many different manufacturers are known in the art and are commercially available. These laser slit lamps are connected via a light-conducting fiber arrangement to an external (remote) laser radiation source generating an acting beam and/or target beam. Laser slit lamps of this kind are also described in patent literature and in other literature, for example, U.S. Pat. No. 5,921,981. In this connection, combinations of a diode laser and slit lamp or an Nd:YAG laser and slit lamp are known, for example.

The usable wavelengths of laser radiation lie in the near infrared and visible spectral regions. Optical zoom systems in the link system or applicator are used for adjusting spot sizes. Pulsed operation of the acting beam sources, for example, by intensity modulation of the pump source, is also known.

The loss of radiation power occurring along the path from the radiation source through the slit lamp to the patient has turned out to be a substantial disadvantage in known laser slit lamps. In order to eliminate these disadvantages, it would be necessary to compensate for the transfer loss through higher optical and electrical source outputs.

Other disadvantages include the high number of electric connection lines between the laser radiation source and the applying system (laser slit lamp), high setup costs, and long light transfer via a sensitive light-conducting fiber to the applying system (laser slit lamp or link system).

OBJECT AND SUMMARY OF THE INVENTION

It is the primary object of the invention to provide a medical laser therapy device which makes it possible to provide and apply laser radiation of different wavelengths for different applications in a simple construction by exchanging structural component parts and/or component groups and, accordingly, to enable an effective and careful treatment of areas in or on the eye of a patient.

According to the invention, this object is achieved by the laser therapy device described, for example, on the following page and otherwise below.

The medical laser therapy device primarily comprises the following main components: pump module with a coupling element, laser radiation source or sources, applicator and corresponding beam control system(s) which transmit(s) the laser radiation, wherein the individual main components, in turn, are constructed and positioned in different ways depending upon the application.

The laser therapy device in the embodiments comprises a controllable pump module with a suitable coupling element for a waveguide, a beam control device in the form of a waveguide for supplying the pumping radiation delivered by the pump module to the laser medium and/or to the applicator, and an applicator, possibly with a coupling element for a waveguide, for introducing a target beam and/or treatment beam into the patient's eye which is to be treated.

A laser therapy device of the type mentioned above is characterized in that the pump module has laser diodes whose electromagnetic pumping radiation is in the spectral range from 800 nm to 815 nm, and in that an optics module which serves as a coupling element is provided which couples the pumping radiation into the waveguide, in that the beam control device is an Nd-doped waveguide laser with a double core or single core and a suitable reflecting coating of the fiber end faces, wherein the waveguide forms a laser cavity with radiation in a frequency range between 1050 nm and 1070 nm, in that the applicator is a laser slit lamp with zoom system having a device for frequency doubling which preferably comprises periodically poled nonlinear optical material, wherein this device is arranged inside or outside part of the laser cavity, and in that the applicator has a target beam device whose radiation is coupled collinearly into the beam path for the therapy radiation by a suitable beamsplitter.

For purposes of a simpler and versatile application, it is advantageous when the applicator is constructed as a head ophthalmoscope and a device for frequency doubling comprises a nonlinear optical material, known per se, this device being arrangement inside or outside the cavity. This nonlinear optical material can be a crystal.

The applicator can be constructed as a laser link with a zoom system and can comprise a device for frequency doubling which is made from nonlinear optical material or periodically poled nonlinear material, wherein this device is an internal or external part of the laser cavity.

Another constriction of the laser therapy device comprises a controllable pump module with a coupling element for a waveguide, a beam control device in the form of a waveguide for supplying the pumping radiation delivered by the pump module to the applicator, and an applicator with a coupling element for a waveguide for introducing a target beam and/or treatment beam into the patient's eye which is to be treated. In this respect, it is advantageous when the pump module has laser diodes whose electromagnetic pumping radiation is in the spectral range from 800 nm to 815 nm, and an optics module is provided which couples the pumping radiation into the waveguide, the pump module has a target beam device whose radiation is coupled into the beam path for the therapy radiation collinearly by a suitable beamsplitter, the beam control device is an Nd-doped waveguide laser with a double core or single core and suitable reflecting coating of the fiber end faces, wherein the waveguide forms a laser cavity with radiation in a frequency range between 1050 nm and 1070 nm, the applicator is a laser slit lamp with a zoom system which has a device for frequency doubling comprising nonlinear optical material or periodically poled nonlinear optical material, the applicator has a device for power monitoring and a device for illuminating and observing the operating field.

It is further advantageous that the applicator is a head ophthalmoscope which has a device for frequency doubling preferably comprising nonlinear optical material which can also be periodically poled, wherein this device is an internal or external part of the laser cavity.

The applicator can also be a laser link which has a zoom system and a device for frequency doubling preferably comprising nonlinear optical material which can also be periodically poled, wherein this device can be an internal or external part of the laser cavity.

Another embodiment form of a laser therapy device, according to the invention, is characterized in that the pump module comprises laser diodes whose electromagnetic pumping radiation is in the spectral range from 830 nm to 850 nm, in that an optics module is provided which couples the pumping radiation of the laser diodes into the waveguide, in that the beam control device is constructed as a Pr/Yb-doped waveguide with suitable reflecting coating of the fiber end faces, so that the waveguide forms a laser cavity for radiation in the frequency range between 520 nm and 540 nm or between 630 nm and 640 nm, depending on its technical design, in that the applicator is a laser slit lamp with a zoom system, comprises a device for monitoring power and a device for illuminating and observing the operating field, and in that the applicator has a target beam device whose radiation is coupled into the beam path for the therapy radiation collinearly by a beamsplitter.

In this case also, the applicator can be constructed as a head ophthalmoscope or as a laser link with zoom system.

Another construction of a therapy device which meets the stated object of the invention is characterized in that the pump module comprises laser diodes whose electromagnetic pumping radiation is in the spectral range from 830 nm to 850 nm, and in that an optics module is provided which couples the radiation of the laser diodes into the waveguide, in that the beam control device is constructed as a Pr/Yb-doped waveguide with suitable reflecting coating of the fiber end faces, so that the waveguide forms a laser cavity for radiation in the frequency range between 520 nm and 540 nm or between 630 nm and 640 nm, depending on its technical design, in that the applicator is a laser slit lamp with a zoom system, comprises a device for monitoring power and a device for illuminating and observing the operating field, and in that the pump module comprises a target beam device whose radiation is coupled into the beam path for the pumping radiation collinearly by a beamsplitter.

In this connection, it is advantageous when the applicator is a laser slit lamp with a zoom system or a head ophthalmoscope.

The applicator can also advantageously be a laser link with zoom system.

A therapy device which also meets the above-stated object is characterized in that the pump module comprises laser diodes whose electromagnetic pumping radiation is in the spectral range from 970 nm to 980 nm, and in that an optics module is provided which couples the pumping radiation of the laser diodes into the fiber, in that the beam control device is constructed as an Er-doped waveguide with suitable reflecting coating of the waveguide end faces, so that the waveguide forms a laser cavity for radiation in the frequency range between 540 nm and 550 nm, in that the applicator is a laser slit lamp with a zoom system, in that the applicator comprises a device for monitoring power, in that the applicator comprises a device for illuminating and observing the operating field, and in that the applicator comprises a target beam device whose radiation is coupled into the beam path for the therapy radiation collinearly by a beamsplitter.

In this case, the applicator is also advantageously a head ophthalmoscope or a laser link with zoom system.

In another modification of a laser therapy device according to the invention, it is advantageous that the pump module comprises laser diodes whose electromagnetic pumping radiation is in the spectral range from 970 nm to 980 nm and that an optics module is provided which couples the pumping radiation of the laser diodes into the fiber, the beam control device is constructed as an Er-doped waveguide with suitable reflecting coating of the waveguide end faces, so that the waveguide forms a laser cavity for radiation in the frequency range between 540 nm and 550 nm, the applicator is a laser slit lamp with a zoom system, the applicator comprises a device for monitoring power and a device for illuminating and observing the operating field, and the pump module comprises a target beam device whose radiation is coupled into the beam path for the pumping radiation collinearly by a suitable beamsplitter.

In this device, also, the applicator is advantageously a laser slit lamp with zoom system. However, it can also be constructed as a head ophthalmoscope.

Further, the applicator can be a laser link with zoom system.

Another laser therapy device, constructed according to the invention, for medical applications comprises a controllable pump module with a coupling element for a waveguide, a beam control device in the form of a waveguide for supplying the pumping radiation delivered by the pump module to the applicator, and an applicator with a coupling element for the waveguide for introducing a target beam and/or treatment beam into the patient's eye which is to be treated. The therapy device is further characterized in that the pump module has laser diodes whose electromagnetic pumping radiation is in the spectral range from 800 nm to 815 nm, and in that an optics module is provided which couples the pumping radiation into the waveguide, in that the beam control device is a non-doped waveguide, possibly with antireflection-coated end faces, so that the pumping radiation is supplied to the applicator, in that the applicator is a laser slit lamp with zoom system which comprises a microchip laser for converting the pumping radiation into radiation in the green spectral range, in that the applicator has a device for monitoring power and a device for illuminating and observing the operating field, and in that the applicator has a target beam device whose radiation is coupled into the beam path for the therapy radiation collinearly by a beamsplitter.

Accordingly, it is advantageous that the applicator is a head ophthalmoscope which comprises a microchip laser for converting the pumping radiation into radiation in the green spectral range.

The applicator can also be a laser link with a zoom system and with a microchip laser for converting the pumping radiation into radiation in the green spectral range.

According to another construction of the invention, the following characterizing features are provided:

the pump module comprises laser diodes whose electromagnetic pumping radiation is in the spectral range from 800 nm to 815 nm, and an optics module is provided which couples the pumping radiation into the waveguide; the beam control device is a non-doped waveguide, possibly with antireflection-coated end faces, so that the pumping radiation is supplied to the applicator; the applicator is a laser slit lamp with zoom system which comprises a microchip laser for converting the pumping radiation into radiation in the green spectral range; the applicator has a device for monitoring power and a device for illuminating and observing the operating field; the pump module has a target beam device whose radiation is coupled into the beam path for the pumping radiation collinearly by a suitable beamsplitter; the applicator is a laser slit lamp with zoom system which comprises a microchip laser for converting the pumping radiation into radiation in the green spectral range.

In this connection, the applicator is advantageously a head ophthalmoscope which comprises a microchip laser for converting the pumping radiation into radiation in the green spectral range.

The applicator can also be a laser link with zoom system which comprises a microchip laser for converting the pumping radiation into radiation in the green spectral range.

For purposes of a versatile, all-purpose application of the laser therapy device, it is particularly advantageous when the applicator is constructed as a handpiece for endoscopic or cyclophotocoagulation ("CPC") applications to which is connected a beam control device in the form of a waveguide.

Generally, it is advantageous in all applications when the pump module optionally comprises a measuring device for calibrating internal output regulation.

The invention will be explained more fully in the following with reference to embodiment examples.

DESCRIPTION OF THE PREFERRED EMBODIMENTS

Identical elements and identical component groups are identified by identical reference numbers in the individual Figures. The examples are described with reference to an applicator with slit lamp. Instead of the slit lamp, a head ophthalmoscope, a link system LS or a correspondingly constructed handpiece can also be used.

Figure 1:
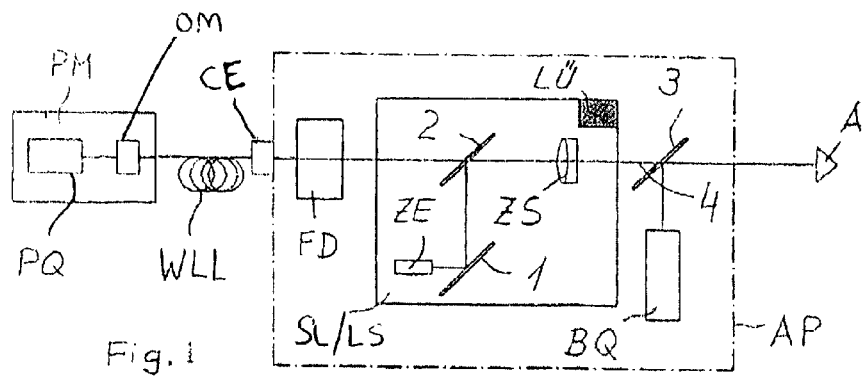
FIGS. 1 to 8 show schematic block diagrams of different embodiment examples of a medical therapy device in modular construction.

The medical laser therapy device, in particular for application in ophthalmology, which is illustrated as a block diagram in FIG. 1 comprises a pump module PM which, in turn, comprises a pumping radiation source PQ emitting pumping radiation in a wavelength range from 780 nm to 815 nm. This pump module PM is connected, preferably by a coupling element (shown as optics module OM), to a waveguide laser WLL which emits radiation in the wavelength range from 1050 nm to 1070 nm and which is abeam control device in the form of a single-core or double-core waveguide, known per se. This waveguide comprises a core of material which is doped with laser-active ions $Nd^{3+}$, the end faces of the waveguide being constructed as a cavity mirror corresponding to the wavelength of the radiation.

The radiation emitted by the waveguide laser WLL is supplied to an applicator AP which is arranged downstream, possibly with the intermediary of a suitable coupling element CE, and which can be constructed in various ways. In FIG. 1, it is shown as a block identified by a dash-dot line. The applicator AP further includes a frequency doubler FD comprising a nonlinear, optical crystal, known per se, which doubles the frequency of the laser radiation and which is arranged downstream of the waveguide laser WLL, and a slit lamp SL with a slit lamp microscope and zoom system ZS and a device LU for measuring and monitoring the power of the emitted radiation.

In this embodiment form of the therapy device according to the invention, the slit lamp SL comprises a target beam device ZE which emits a target beam for targeting the location to be treated in or on the eye A, this target beam being coupled into the beam path for the therapy radiation collinearly by deflecting means 1 and a suitable beamsplitter 2. Accordingly, it is always ensured that the target beam and therapy beam strike the location to be treated in or on the eye A together. In other arrangements, it may be advantageous to unite the illumination in noncollinear fashion with the therapy beam in the operating field in order to prevent impairment of the therapy beam by the beamsplitter 3.

As can be seen further from FIG. 1, the applicator AP comprises an illumination beam source BQ whose emitted radiation is coupled into the beam path 4 exiting the applicator AP collinearly via another beamsplitter 3. In this way, an illumination of the location to be irradiated is also realized, so that a visual observation is also made possible through the slit lamp microscope.

The provided zoom system ZS serves to change the cross section of the therapy beam and, therefore, the adjustment of the spot size on the irradiated location. It is also advantageous when the applicator AP has an arrangement for power monitoring LU of the delivered radiation.

The applicator AP itself can be constructed as a slit lamp SL or as a head ophthalmoscope, link system LS or handpiece.

The therapy device according to FIG. 1 can also comprise an Er-doped waveguide laser WLL which is pumped by a pumping radiation of wavelengths between 970 nm and 980 nm and which emits radiation in the range from 540 nm to 550 nm.

Figure 2:
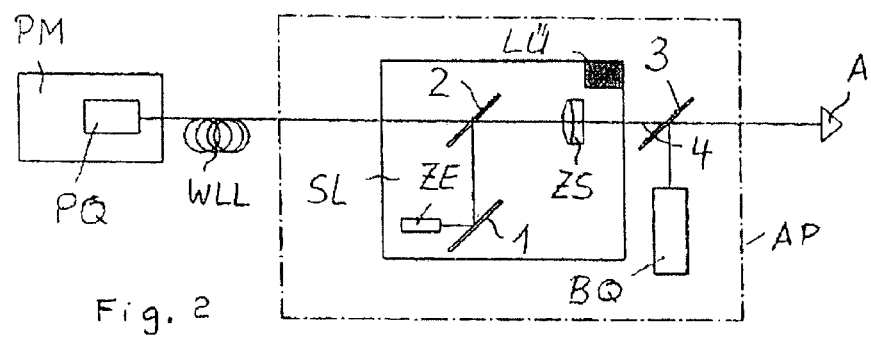

In the laser therapy device shown in FIG. 2, a pumping radiation source PQ which emits a radiation in the range from 830 nm to 850 nm is provided in the pump module. The waveguide laser WLL which is provided as therapy radiation source has an Nd/Pr-doped fiber core and emits radiation in the visible wavelength range from 520 nm to 540 nm or 630 nm to 640 nm, so that frequency doubling of the radiation is obviated and a frequency doubler is not provided.

Figure 3:
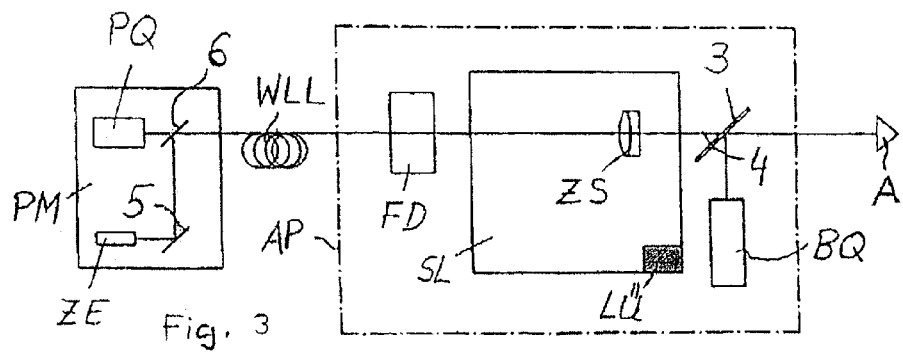

Aside from the pumping radiation source PQ, the pump module PM in the therapy device according to FIG. 3 also comprises the target beam device ZE whose radiation is coupled into the pumping beam by a deflecting mirror 5 and a beamsplitter 6 and conveyed further into the Nd-doped waveguide laser WLL. The wavelength of the waveguide laser WLL is 1050 nm to 1070 nm and the wavelength of the pumping radiation is ill the range from 780 nm to 815 nm. Since the wavelength of the radiation emitted by the waveguide laser WLL is not in the visible region of the spectrum, a frequency doubler FD is arranged in the applicator AP downstream of the laser. The slit lamp SL comprises the zoom system ZS and the device for power monitoring LU. The beam of the illumination radiation source BQ is coupled into the beam path 4 by the beamsplitter 3 and is further conveyed into the eye A; this in-coupling can be carried out in collinear or non-collinear manner.

Figure 4:
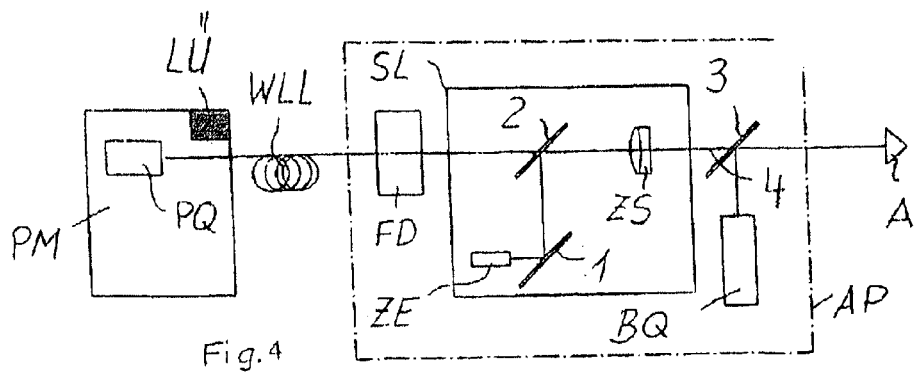

In the device according to FIG. 4, the device for power monitoring LU and the pumping radiation source PQ are arranged in the pump module PM. The target beam device ZE is located in the slit amp SL which is a component part of the applicator AP. The pumping radiation source PQ emits radiation in the range from 780 nm to 815 nm. The waveguide laser WLL is Nd-doped. Its emitted therapy radiation has wavelengths from 1050 nm to 1070 nm; therefore, a frequency doubler FD is arranged after it. As in the device according to FIGS. 1 to 3, the zoom system ZS is located in the sit lamp SL. The illumination radiation source BQ is arranged in the applicator AP. Its radiation is again coupled into the beam path 4 through the beamsplitter 3. This can be carried out in collinear or non-collinear manner.

Figure 5:
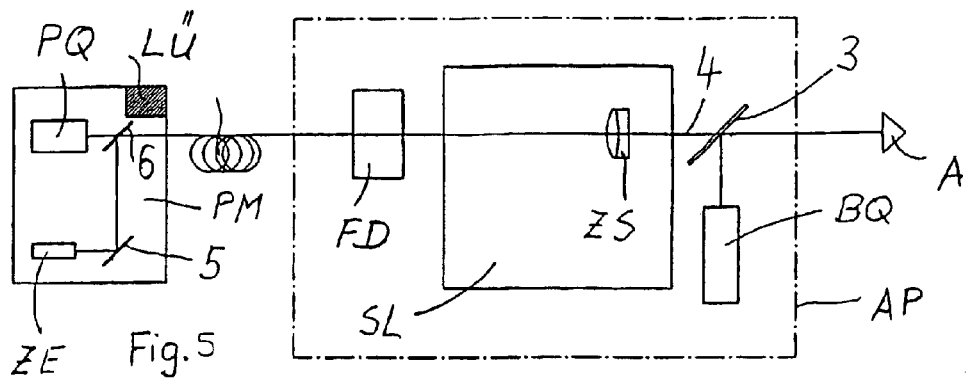

In the therapy device shown in FIG. 5, the pump module PM comprises the pumping radiation source PQ, the target beam device ZE and the device for power monitoring LU. The target beam is coupled into the pumping beam by the deflecting mirror 5 and the beamsplitter 6. The pumping radiation source PQ emits radiation in the range from 780 nm to 815 nm. The waveguide laser WLL is doped with Nd. The therapy radiation emitted by it has wavelengths from 1050 nm to 1070 nm; therefore, a frequency doubler VD is arranged after it. The zoom system ZS is arranged in the slit lamp SL. Aside from the frequency doubler VD, the applicator AP also comprises the slit lamp SL and the illumination radiation source BQ and the beamsplitter 3.

Figure 6:
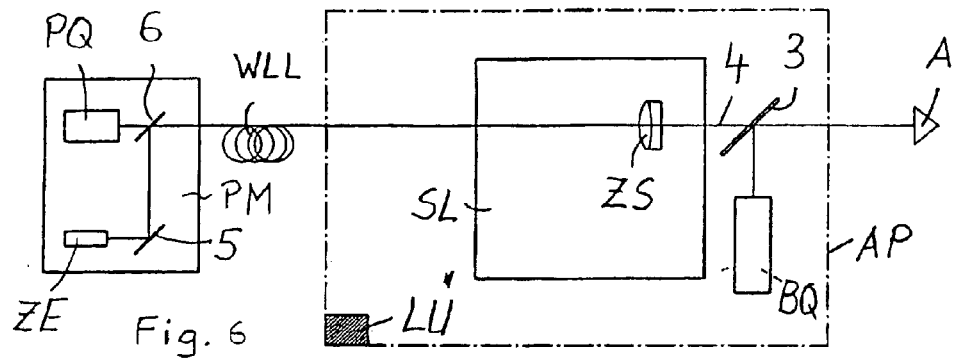

FIG. 6 shows a medical therapy device with a pump module PM which is constructed identical to the module shown in FIG. 3. The pumping radiation source PQ emits a pumping radiation in the wavelength range from 830 nm to 850 nm. The radiation of the Pr/Yb-doped waveguide laser WLL is in the range from 520 nm to 540 nm or 630 nm to 640 nm, depending on its technical construction. With this device it is also possible, for example, to provide a pumping radiation source PQ with pumping radiation of a wavelength of 970 nm to 980 nm and to provide an Er-doped waveguide laser WLL which emits radiation in a wavelength range from 540 nm to 550 nm. The applicator AP comprises the slit lamp SL with zoom system ZS, the illumination radiation source BQ and the device for power monitoring LU. The light of the illumination radiation source BQ is also coupled into the beam path 4 in a collinear or non-collinear manner by the beamsplitter 3.

Figure 7:
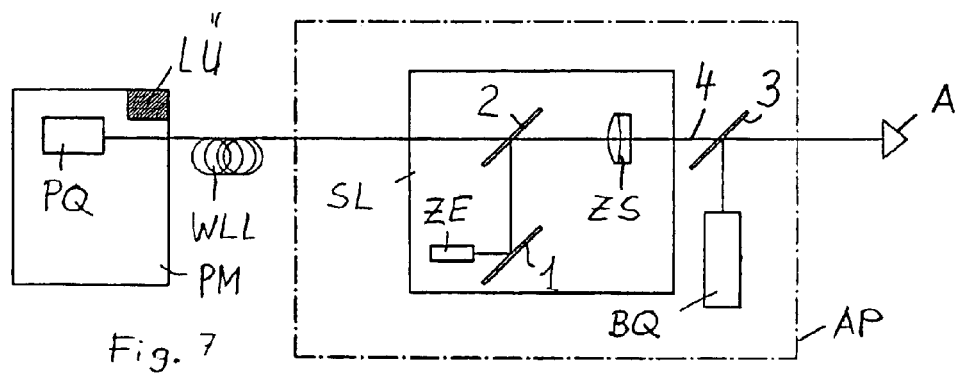

The medical therapy device according to FIG. 7 comprises a pump module PM with the pumping radiation source PQ and the device for power monitoring LU. The pumping radiation source PQ emits a pumping radiation in the wavelength range from 830 nm to 850 nm. The radiation of the Pr/Yb-doped waveguide laser WLL is in the range from 520 run to 540 nm or 630 nm to 640 nm. With this device it is also possible, for example, to provide a pumping radiation source PQ with pumping radiation of a wavelength of 970 nm to 980 nm and to provide an Er-doped waveguide laser WLL which emits radiation in a wavelength range from 540 nm to 550 nm. A frequency doubler is not required in this construction. The target beam device ZE is located in the slit lamp SL. The deflecting means 1 and the beamsplitter 2 are provided for collinear coupling of the target beam into the therapy beam and are arranged in front of the zoom system ZS in the radiating direction. The zoom system ZS is likewise arranged in the slit lamp SL. In this case, the illumination radiation is coupled into the beam path exiting the applicator AP in the manner described further above.

Figure 8:
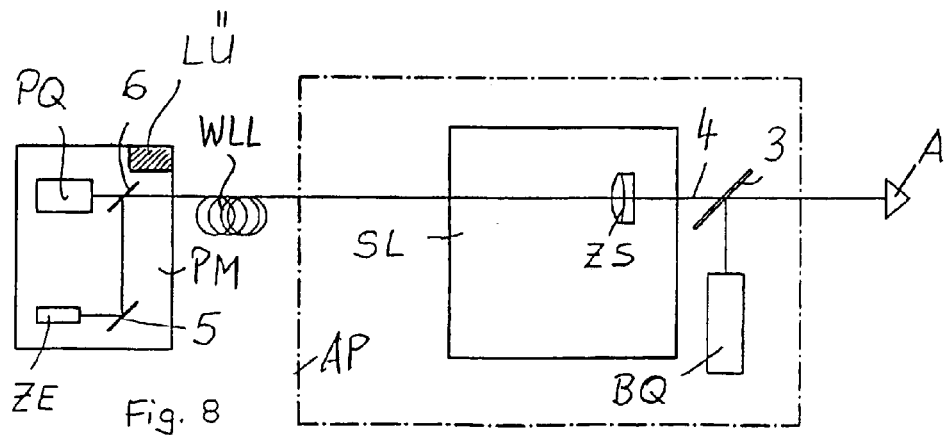

The therapy device shown in FIG. 8 as a block diagram differs from that shown in FIG. 5 only in that there is no frequency doubler in the device according to FIG. 8. Such a frequency doubler is also not required, since the waveguide laser WLL emits radiation in a wavelength range that is favorable and required for therapy, so that frequency doubling can be dispensed with. The pumping radiation source PQ emits a pumping radiation in the wavelength range from 830 nm to 850 nm. The radiation of the Pr/Yb-doped waveguide laser WLL is in the range from 520 nm to 540 nm or 630 nm to 640 nm. With this device it is also possible, for example, to provide a pumping radiation source PQ with pumping radiation of a wavelength of 970 nm to 980 nm and to provide an Er-doped waveguide laser WLL which emits radiation in a wavelength range from 540 nm to 550 nm. As concerns the rest of the construction, reference is had to the description relating to FIG. 5.

For purposes of a versatile, all-purpose application of the laser therapy device, it is particularly advantageous when the applicator is constructed as a handpiece for endoscopic or CPC applications, a beam control device in the form of a waveguide being connected to this handpiece.

Generally, it is advantageous in all applications when the pump module optionally comprises a measuring device for calibrating the internal power regulation.

The medical therapy device according to the invention is constructed in modular manner and makes it possible to provide and apply laser radiation of different wavelengths for different applications in a simple construction by exchanging structural component parts and/or component groups and, accordingly, to enable an effective and careful treatment particularly of areas in or on the eye of a patient.

While the foregoing description and drawings represent the present invention, it will be obvious to those skilled in the art that various changes may be made therein without departing from the true spirit and scope of the present invention.

What is claimed is:

1. A medical laser therapy device comprising:
   a controllable pump module with a coupling element for a waveguide;
   an applicator with a coupling element for the waveguide for introducing a target beam and/or treatment beam into an eve to be treated;
   a beam control device in the form of a waveguide for supplying the pumping radiation delivered by the pump module to the applicator;
   said pump module having laser diodes whose electromagnetic pumping radiation is in the spectral range from 800 nm to 815 nm;
   an optics module being provided which couples the pumping radiation into the waveguide;
   said beam control device being an Nd-doped waveguide laser with a double core or single core and a suitable reflecting coating of the fiber end faces;
   said waveguide forming a laser cavity with radiation in a frequency range between 1050 nm and 1070 nm;
   said applicator being a laser slit lamp with zoom system having a device for frequency doubling which comprises nonlinear optical material or periodically poled nonlinear optical material;

said applicator having a device for power monitoring;
said applicator having a device for illuminating and observing the operating field; and
said applicator also having a target beam device whose radiation is coupled collinearly into the beam path for the therapy radiation by a suitable beamsplitter.

2. The laser therapy device according to claim 1, wherein the applicator is constructed as a head ophthalmoscope with a device for frequency doubling comprising a nonlinear optical material or periodically poled nonlinear optical material.

3. The laser therapy device according to claim 1, wherein the applicator is a laser link with a zoom system and has a device for frequency doubling which is made from nonlinear optical material or periodically poled nonlinear material, wherein this device is an internal or external part of the laser cavity.

4. A laser therapy device comprising:
a controllable pump module with a coupling element for a waveguide;
an applicator with a coupling element for the waveguide for introducing a target beam and/or treatment beam into an eye to be treated;
a beam control device in the form of a waveguide for supplying the pumping radiation delivered by the pump module to the applicator;
said pump module having laser diodes whose electromagnetic pumping radiation is in the spectral range from 800 nm to 815 nm;
an optics module being provided which couples the pumping radiation into the waveguide;
said pump module having a target beam device whose radiation is coupled into the beam path for the therapy radiation collinearly by a suitable beamsplitter;
said beam control device being an Nd-doped waveguide laser with a double core or single core and suitable reflecting coating of the fiber end faces, wherein the waveguide forms a laser cavity with radiation in a frequency range between 1050 nm and 1070 nm;
said applicator being a laser slit lamp with a zoom system which has a device for frequency doubling comprising nonlinear optical material or periodically poled nonlinear optical material; and
said applicator having a device for power monitoring; and
said applicator also having a device for illuminating and observing the operating field.

5. The laser therapy device according to claim 4, wherein the applicator is a head ophthalmoscope which has a device for frequency doubling preferably comprising nonlinear optical material which can also be periodically poled, wherein this device is an internal or external part of the laser cavity.

6. The laser therapy device according to claim 4, wherein the applicator is a laser link which has a zoom system and a device for frequency doubling preferably comprising nonlinear optical material which can also be periodically poled, wherein this device can be an internal or external part of the laser cavity.

7. A laser therapy device for medical applications comprising:
a controllable pump module with a coupling element for a waveguide;
an applicator with a coupling element for the waveguide for introducing a target beam and/or treatment beam into an eye to be treated;
a beam control device in the form of a waveguide for supplying the pumping radiation delivered by the pump module to the applicator; and
said pump module comprising laser diodes whose electromagnetic pumping radiation is in the spectral range from 830 nm to 850 nm;
an optics module being provided which couples the pumping radiation of the laser diodes into the waveguide;
said beam control device being constructed as a Pr/Yb-doped waveguide with suitable reflecting coating of the fiber end faces, so that the waveguide forms a laser cavity for radiation in the frequency range between 520 nm and 540 nm or between 630 nm and 640 nm, depending on its technical design;
said applicator being a laser slit lamp with a zoom system and comprising a device for monitoring power and a device for illuminating and observing the operating field; and
said applicator having a target beam device whose radiation is coupled into the beam path for the therapy radiation collinearly by a beamsplitter.

8. The laser therapy device according to claim 7, wherein the applicator is a head ophthalmoscope.

9. The laser therapy device according to claim 7, wherein the applicator is a laser link with a zoom system.

10. A laser therapy device comprising:
an applicator with a coupling element for the waveguide for introducing a target beam and/or treatment beam into an eve to be treated;
a controllable pump module with a coupling element for a waveguide, a beam control device in the form of a waveguide for supplying the pumping radiation delivered by the pump module to the applicator; and
said pump module comprising laser diodes whose electromagnetic pumping radiation is in the spectral range from 830 nm to 850 nm;
an optics module being provided which couples the radiation of the laser diodes into the waveguide;
said beam control device being constructed as a Pr/Yb-doped waveguide with suitable reflecting coating of the fiber end faces, so that the waveguide forms a laser cavity for radiation in the frequency range between 520 nm and 540 nm or between 630 nm and 640 nm, depending on its technical design;
said applicator being a laser slit lamp with a zoom system;
said applicator comprising a device for monitoring power and a device for illuminating and observing the operating field; and
said pump module comprising a target beam device whose radiation is coupled into the beam path for the pumping radiation collinearly by a beamsplitter.

11. The laser therapy device according to claim 10, wherein the applicator is a head ophthalmoscope.

12. The laser therapy device according to claim 10, wherein the applicator is a laser link with zoom system.

13. A laser therapy device for medical applications comprising:
a controllable pump module with a coupling element for a waveguide;
an applicator with a coupling element for the waveguide for introducing a target beam and/or treatment beam into an eve to be treated;
a beam control device in the form of a waveguide for supplying the pumping radiation delivered by the pump module to the applicator; and
said pump module comprising laser diodes whose electromagnetic pumping radiation is in the spectral range from 970 nm to 980 nm;
an optics module being provided which couples the pumping radiation of the laser diodes into the fiber;

said beam control device being constructed as an Er-doped waveguide with suitable reflecting coating of the waveguide end faces, so that the waveguide forms a laser cavity for radiation in the frequency range between 540 nm and 550 nm;

said applicator being a laser slit lamp with a zoom system;

said applicator comprising a device for monitoring power;

said applicator comprising a device for illuminating and observing the operating field; and said applicator comprising a target beam device whose radiation is coupled into the beam path for the therapy radiation collinearly by a beamsplitter.

14. The laser therapy device according to claim 13, wherein the applicator is a head ophthalmoscope.

15. The laser therapy device according to claim 13, wherein the applicator is a laser link with zoom system.

16. A laser therapy device comprising:

a controllable pump module with a coupling element for a waveguide;

an applicator with a coupling element for the waveguide for introducing a target beam and/or treatment beam into an eve to be treated;

a beam control device in the form of a waveguide for supplying the pumping radiation delivered by the pump module to the applicator;

said pump module comprising laser diodes whose electromagnetic pumping radiation is in the spectral range from 970 nm to 980 nm;

an optics module being provided which couples the pumping radiation of the laser diodes into the fiber;

said beam control device being constructed as an Er-doped waveguide with suitable reflecting coating of the waveguide end faces, so that the waveguide forms a laser cavity for radiation in the frequency range between 540 nm and 550 nm;

said applicator being a laser slit lamp with a zoom system;

said applicator comprising a device for monitoring power;

said applicator having a device for illuminating and observing the operating field; and said pump module comprising a target beam device whose radiation is coupled into the beam path for the pumping radiation collinearly by a suitable beamsplitter.

17. The laser therapy device according to claim 16, wherein the applicator is a head ophthalmoscope.

18. The laser therapy device according to claim 16, wherein the applicator is a laser link with zoom system.

19. The laser therapy device for medical applications comprising:

a controllable pump module with a coupling element for a waveguide;

an applicator with a coupling element for the waveguide for introducing a target beam and/or treatment beam into eve to be treated;

a beam control device in the form of a waveguide for supplying the pumping radiation delivered by the pump module to the applicator; and said pump module having laser diodes whose electromagnetic pumping radiation is in the spectral range from 800 nm to 815 nm; and an optics module being provided which couples the pumping radiation into the waveguide, in that the beam control device is a non-doped waveguide, so that the pumping radiation is supplied to the applicator;

said applicator being a laser slit lamp with zoom system which comprises a microchip laser for converting the pumping radiation into radiation in the green spectral range;

said applicator having a device for monitoring power and a device for illuminating and observing the operating field; and said applicator having a target beam device whose radiation is coupled into the beam path for the therapy radiation collinearly by a beamsplitter.

20. The laser therapy device according to claim 19, wherein the applicator is a head ophthalmoscope which comprises a microchip laser for converting the pumping radiation into radiation in the green spectral range.

21. The laser therapy device according to claim 19, wherein the applicator is a laser link with a zoom system and with a microchip laser for converting the pumping radiation into radiation in the green spectral range.

22. A laser therapy device comprising:

a controllable pump module with a coupling element for a waveguide;

an applicator with a coupling element for the waveguide for introducing a target beam and/or treatment beam into an eve to be treated;

a beam control device in the form of a waveguide for supplying the pumping radiation delivered by the pump module to the applicator; and said pump module comprising laser diodes whose electromagnetic pumping radiation is in the spectral range from 800 nm to 815 nm; and an optics module being provided which couples the pumping radiation into the waveguide;

said beam control device being a non-doped waveguide, so that the pumping radiation is supplied to the applicator;

said applicator being a laser slit lamp with zoom system which comprises a microchip laser for converting the pumping radiation into radiation in the green spectral range;

said applicator having a device for monitoring power and a device for illuminating and observing the operating field;

said pump module having a target beam device whose radiation is coupled into the beam path for the pumping radiation collinearly by a suitable beamsplitter;

said applicator being a laser slit lamp with zoom system which comprises a microchip laser for converting the pumping radiation into radiation in the green spectral range.

23. The laser therapy device according to claim 22, wherein the applicator is a head ophthalmoscope which comprises a microchip laser for converting the pumping radiation into radiation in the green spectral range.

24. The laser therapy device according to claim 22, wherein the applicator is a laser link with zoom system which comprises a microchip laser for converting the pumping radiation into radiation in the green spectral range.

25. The laser therapy device according to claim 22, wherein the pump module optionally comprises a measuring device for calibrating internal power regulation.

26. The laser therapy device according to claim 22, wherein the applicator is constructed as a handpiece for endoscopic or cyclophotocoagulation (CPC) applications.

* * * * *